United States Patent
Schappacher (10) Patent No.: US 9,733,124 B2
(45) Date of Patent: Aug. 15, 2017

(54) MICROPLATE READER WITH LINEAR VARIABLE FILTER

(71) Applicant: BMG LABTECH, GmbH, Ortenberg (DE)

(72) Inventor: Markus Schappacher, Oberkirch (DE)

(73) Assignee: BMG LABTECH, GmbH, Ortenberg (DE)

( * ) Notice: Subject to any disclaimer, the term of this patent is extended or adjusted under 35 U.S.C. 154(b) by 566 days.

(21) Appl. No.: 14/250,589

(22) Filed: Apr. 11, 2014

(65) Prior Publication Data

US 2014/0312212 A1    Oct. 23, 2014

Related U.S. Application Data

(60) Provisional application No. 61/813,409, filed on Apr. 18, 2013.

(51) Int. Cl.
| | |
|---|---|
| *H01J 5/16* | (2006.01) |
| *G01J 3/02* | (2006.01) |
| *G01J 3/12* | (2006.01) |
| *G01J 3/26* | (2006.01) |
| *G01N 21/25* | (2006.01) |
| *G01N 21/64* | (2006.01) |

(52) U.S. Cl.
CPC .............. *G01J 3/0224* (2013.01); *G01J 3/12* (2013.01); *G01J 3/26* (2013.01); *G01N 21/253* (2013.01); *G01N 21/6452* (2013.01); *G01J 2003/1213* (2013.01); *G01J 2003/1221* (2013.01); *G01J 2003/1234* (2013.01); *G01N 2021/6471* (2013.01)

(58) Field of Classification Search
CPC ........ G01J 3/12; G01J 3/26; G01J 3/50; G01J 3/0224; G01J 2003/1213; G01J 2003/1234; G01N 21/253; G01N 21/6452
USPC ......................................................... 250/226
See application file for complete search history.

(56) References Cited

U.S. PATENT DOCUMENTS

| | | | |
|---|---|---|---|
| 5,784,152 A | 7/1998 | Heffelfinger et al. | |
| 6,160,618 A | 12/2000 | Garner | |
| 6,657,758 B1 | 12/2003 | Garner | |
| 6,700,690 B1 | 3/2004 | Buchsbaum et al. | |
| 7,015,484 B2 | 3/2006 | Gillispie et al. | |
| 9,625,628 B2 * | 4/2017 | Hruska | ................. G02B 5/285 |
| 2003/0058530 A1 * | 3/2003 | Kawano | ............... G02B 21/002 |
| | | | 359/385 |

(Continued)

*Primary Examiner* — Georgia Y Epps
*Assistant Examiner* — Kevin Wyatt
(74) *Attorney, Agent, or Firm* — Coats & Bennett, PLLC (57) ABSTRACT

A microplate reader includes a pair of linear variable filters (LVFs) that together form a wavelength selector. Movement of one or both of the LVFs enables selection of the desired center wavelength and/or passband used to analyze a sample on a microplate inserted into the microplate reader. The microplate reader may also include a similar second wavelength selector. The LVFs are located on movable frames, with each frame also advantageously including least one of an aperture, a fixed optical filter, and an optical polarization filter. In some cases, different types of measurements may be taken without changing the geometry of the optical path between the wavelength selectors. The microplate reader may additionally use a LVF to form a continuously adjustable dichroic for sample analysis.

22 Claims, 7 Drawing Sheets

(56) References Cited

U.S. PATENT DOCUMENTS

2007/0058921 A1* 3/2007 Lundgren ................ G01J 3/02
                                                        385/147

* cited by examiner

MICROPLATE READER WITH LINEAR VARIABLE FILTER

This application claims priority to Provisional U.S. Patent Application 61/813,409 filed 18 Apr. 2013, the disclosure of which is incorporated herein by reference in its entirety.

BACKGROUND

Microplates have become the standard sample container for laboratory testing, taking over the role previously occupied by test tubes and plastic tube arrays. The flat matrix style microplate format is adaptable to a wide range of sample volumes, is convenient for large numbers of samples, and lends itself to various methods of analysis. Microplates are continually evolving and have been constructed of thin film continuous plastic sheets allowing a vast number of plates to be rolled up in a very small volume that contain millions of samples.

Microplate readers primarily comprise optical measurement devices that use standard analytical techniques to probe a sample in a microplate well of a microplate. The samples in the microplate well have intrinsic properties that can be measured using these optical and analytical methods. The samples, or chemicals that can interact with the samples, may alternatively be tagged with compounds or molecules that can be probed using the microplate reader. Exemplary core optical techniques commonly used in microplate readers include: absorbance (ABS), Fluorescence Intensity (FI), luminescence (LUM), Fluorescence Polarization (FP), Time-Resolved Fluorescence (TRF), Fluorescence Lifetime (FLT), Fluorescent (or Förster) Resonance Energy Transfer (FRET), Time-Resolved FRET (TR-FRET), Bioluminescence Resonance Energy Transfer (BRET), nephelometry, Surface Plasmon Resonance (SPR), Alpha Technology (AlphaScreen™, AlphaLISA™), Raman scattering, turbidity (Mie scattering, Rayleigh scattering), and combinations of these, but any analytical optical technique can be adapted to a microplate reader.

While a number of microplate reader designs are available, many have proven unsuitable for some task(s). As such, there remains a need for alternative microplate reader designs.

SUMMARY

The microplate reader disclosed herein uses one or more pairs of linear variable filters to form one or more wavelength selectors, in the excitation stage and/or in the emission stage of the microplate reader, which can be used to select the desired wavelength(s) for sample analysis. The microplate reader may additionally use a linear variable filter to form a continuously adjustable dichroic for sample analysis. In some embodiments, the microplate reader may combine fixed optical filter, spectrometer, and wavelength selection technologies in one microplate reader. The linear variable filters are disposed on respective movable frames (e.g., slides) that include at least one of fixed optical filters, apertures, and optical polarization filters, and the movable frames can be positioned relative to one another for optimal performance.

As exemplary microplate reader comprises a light source, a detector, an optical system, and a first wavelength selector. The light source is configured to emit light at one or more wavelengths, and the detector is configured to detect incident light. The optical system comprises a plurality of optical elements configured to guide the light emitted by the light source along an optical path of the microplate reader from the light source to a microplate, and from the microplate to the detector. The first wavelength selector comprises a first pair of linear variable filters disposed in the optical path. The first pair of linear variable filters comprise first and second linear variable filters, where the first linear variable filter is movable transverse to the optical path and relative to the second linear variable filter. The first linear variable filter is disposed on a first movable frame, with the first movable frame further having at least one of an aperture, a fixed optical filter, and an optical polarization filter disposed thereon. Likewise, the second linear variable filter is disposed on a second movable frame, distinct from the first movable frame, with the second movable frame further having at least one of an aperture, a fixed optical filter, and an optical polarization filter disposed thereon. The first wavelength selector is configured such that movement of at least one of the first and second linear variable filters, transverse to the optical path, adjusts at least one of a first center wavelength and a first bandwidth of the first wavelength selector over a continuous range of wavelengths. When disposed between the light source and the microplate, the first wavelength selector comprises an excitation wavelength selector. When disposed between the microplate and the detector, the first wavelength selector comprises an emission wavelength selector.

In one or more embodiments, the microplate reader includes a second wavelength selector, with the first wavelength selector disposed optically between the light source and the microplate, and the second wavelength selector disposed optically between the microplate and the detector. The second wavelength selector includes a second pair of linear variable filters disposed in the optical path. The second pair of linear variable filters includes third and fourth linear variable filters, with the third linear variable filter movable transverse to the optical path and relative to the fourth linear variable filter. The third linear variable filter is disposed on a third movable frame, the third movable frame further having at least one of an aperture, a fixed optical filter, and an optical polarization filter disposed thereon. The fourth linear variable filter is disposed on a fourth movable frame, distinct from the third movable frame, the fourth movable frame further having at least one of an aperture, a fixed optical filter, and an optical polarization filter disposed thereon. Movement of at least one of the third and fourth linear variable filters transverse to the optical path adjusts at least one of a second center wavelength and a second bandwidth of the second wavelength selector over the continuous range of wavelengths. The microplate reader also includes a dichroic optical element disposed between the light source, the detector, and the microplate so as to direct the light emitted by the light source to the microplate, and to direct the light from the microplate to the detector. The dichroic optical element advantageously comprises a fifth linear variable filter disposed on a fifth movable frame, with the fifth movable frame further having at least one of an aperture and a fixed dichroic mirror disposed thereon.

A first variably sized set of linear variable filters includes one or more of the first, second, third, fourth, and fifth linear variable filters. The microplate reader is advantageously configured to perform both of the following without changing a geometry of the optical path from a point upstream of the first wavelength selector through to a point downstream of the second wavelength selector: a) take a first measurement based on light detected from a well of the microplate while all members of the first set of linear variable filters are disposed in the optical path; b) take a second subsequent measurement based on light detected from the well of the microplate while at least one member of the first set of linear variable filters is disposed not in the optical path. The sequence of the first and second measurements may be reversed.

An exemplary method of adjusting optical properties of a microplate reader is also disclosed, where the microplate reader comprises a light source, a detector, and an optical system comprising a plurality of optical elements configured to guide light emitted by the light source along an optical path from the light source to a microplate, and from the microplate to the detector. The method comprises positioning a first wavelength selector comprising a first pair of linear variable filters in the optical path, where the first wavelength selector comprises an excitation wavelength selector disposed between the light source and the microplate or an emission wavelength selector disposed between the microplate and the detector. The first pair of linear variable filters comprises first and second linear variable filters, with the first linear variable filter movable transverse to the optical path and relative to the second linear variable filter. The method further comprises adjusting at least one of a first center wavelength and a first bandwidth of the first wavelength selector over a continuous range of wavelengths by moving at least one of the first and second linear variable filters transverse to the optical path. Other methods are also described, which may include use of a second wavelength selector and a dichroic optical element as described above.

Advantageously, the method may include detecting light from a well of the microplate while all members of the first set of linear variable filters are disposed in the optical path; and thereafter, without changing a geometry of the optical path from a point upstream of the first wavelength selector through to a point downstream of the second wavelength selector, detecting light from the well of the microplate while at least one member of the first set of linear variable filters is disposed not in the optical path. Or, the presence/absence of the at least one member of the first set of linear variable filters may be reversed.

Other aspects of the assembly and related methods are also evident from the following description and corresponding drawings.

DETAILED DESCRIPTION

Figure 1:
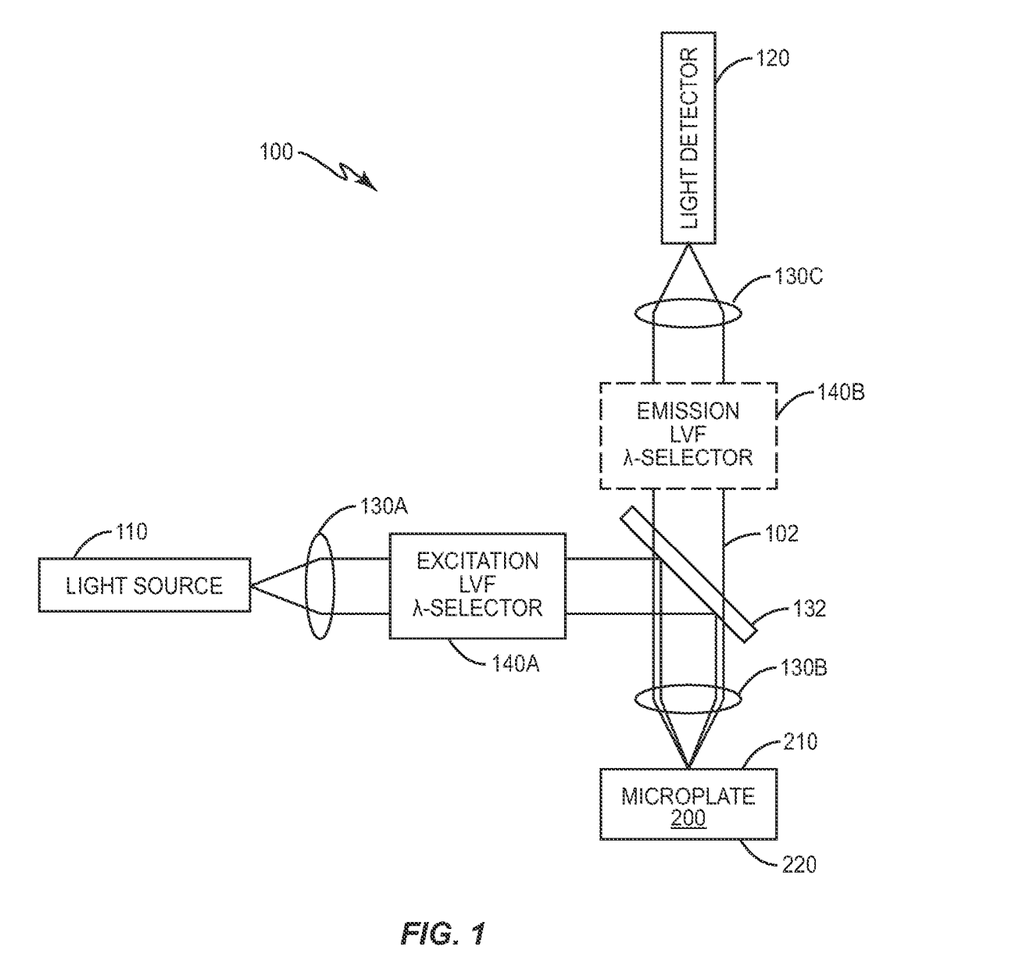
FIG. 1 shows an optical schematic of a microplate reader according to one exemplary embodiment.

FIG. 1 shows an optical schematic of a microplate reader 100 according to one exemplary embodiment. Microplate reader 100 is configured to expose light onto or through a sample disposed on the microplate 200, e.g., in a microplate well, to facilitate testing of the sample. To that end, the microplate reader 100 comprises a light source 110, a light detector 120, an optical system 130, and a wavelength selector 140. The microplate reader 100 comprises an excitation stage along the optical path 102 between the light source 110 and the microplate 200, and an emission stage along the optical path 102 between the microplate 200 and the detector 120.

The light source 110 emits light at one or more wavelengths, while the detector 120 detects incident light. The light source 110 may be any known light source, including but not limited to, a tungsten halogen continuous wave lamp, a deuterium lamp, a xenon flash lamp, light emitting diode(s), a diode laser, a pulsed nitrogen laser, solid state lasers, and any combination of these sources, and may optionally use an optical switch for selection. The detector 120 may comprise any known photosensitive device, including but not limited to, photomultiplier tubes, channel photomultiplier, photodiodes, photocells, linear photodiode arrays, charge coupled devices, and hybrids of these and other photosensitive devices. It will be appreciated that detector 120 may comprise one or more photosensitive devices, where two photosensitive devices may be used, e.g., to improve sensitivity in certain reading modes and/or to increase reading speed, and/or to extend wavelength ranges. While not shown, the output(s) from the detector 120 may be routed to a suitable computing device for analysis according to any known analysis techniques.

The optical system, generally referred to herein with reference number 130, includes optical elements that may include, but are not limited to, lenses, mirrors, beamsplitters, dichroics, blocking filters, shutters, attenuators (e.g., neutral density filters), liquid filled light guides, solid light guides, fiber optic bundles, and optical switches that are used in single or in a variety of combinations to direct light along an optical path 102 to particular components in the microplate reader 100. In the embodiment shown in FIG. 1, the optical system 130 includes multiple optical elements, e.g., optical elements 130A-130C and dichroic 132, which guide and manipulate the light emitted by the light source 110 along the optical path 102 from the light source 110 to the microplate 200, and from the microplate 200 to the detector 120. The optical elements of the exemplary optical system 130 of FIG. 1 include a source optical element 130A, a microplate optical element 130B, and a detector optical element 130C. Source optical element 130A comprises one or more lenses that advantageously collimate the light emitted by the light source 110. Microplate optical element 130B comprises one or more lenses that advantageously focus the collimated light toward a top 210 of the microplate 200, e.g., such that the focused light is incident on a sample in the microplate well of the microplate 200. The microplate optical element 130B may also recollimate the light exiting the top 210 of the microplate 200, e.g., the light that reflects off or is emitted by the sample in the microplate well. While not explicitly shown, the microplate optical element 130B may be moved in or out of the optical path 102 when deemed advantageous for a particular microplate reader operation.

Further, microplate element 130B may also be moved along the optical path to achieve the best focus and/or the highest intensity at the microplate 200. Detector optical element 130C comprises one or more lenses that advantageously focus the collimated light toward the detector 120, e.g., such that the focused light is incident on a surface of the detector 120. Alternatively, the detector element 130C may focus the light on a pinhole (not shown) in front of the detector 120 to allow the construction of a confocal optical system, which may additionally require lens elements between the pinhole and the detector 120.

The wavelength selector, generally referred to herein with reference number 140, selects the desired wavelengths or range of wavelengths for the microplate reader 100. Exemplary wavelength selectors 140 include, but are not limited to, fixed optical filters, grating-based monochromators, prism-based monochromators, and spectrometers. As shown in FIG. 1, the wavelength selector 140 may comprise an excitation wavelength selector 140A disposed in the excitation stage between the light source 110 and the microplate 200. Alternatively, the wavelength selector 140 may comprise an emission wavelength selector 140B disposed in an emission stage between the microplate 200 and the detector 120. It will also be appreciated that the microplate reader 100 may include both an excitation wavelength selector 140A and an emission wavelength selector 140B.

Figure 2:
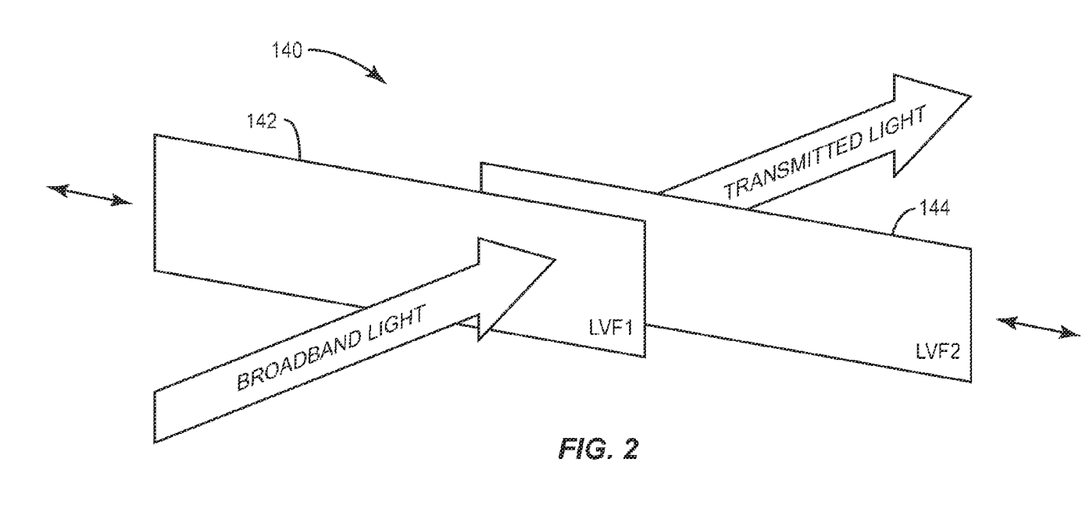
FIG. 2 shows an exemplary pair of linear variable filters arranged in series to form the wavelength selector(s) shown in various other Figures.
Figure 3A:
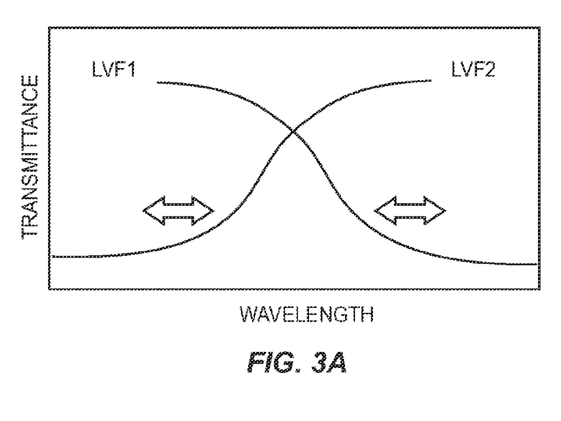
FIGS. 3A and 3B show transmittance graphs for the linear variable filters and wavelength selector of FIG. 2.

For the microplate reader 100 disclosed herein, the wavelength selector 140 may advantageously utilize one or more linear variable filters (LVFs) to add reliable analytic flexibility to the microplate reader 100. In general, LVFs are filters that have a continuously variable coating along their length that variably rejects or passes a certain wavelength of light, with the wavelength of the rejected or passed light being dependent on where the incident light impinges the surface of the LVF. See U.S. Pat. No. 6,700,690. The wavelength selector 140 may advantageously combine two such LVFs, LVF1 142 and LVF2 144, to form a wavelength selector 140 that operates as a monochromater to filter a broadband light source, e.g., light source 110, thus allowing select wavelengths to be transmitted, where the transmitted wavelengths have a certain peak shape and passband (bandwidth of the passed light), both of which may be tunable. FIG. 2 shows an exemplary wavelength selector 140 comprising a pair of LVFs 142, 144 disposed in the optical path 102. As shown in FIG. 3A, LVF1 142 comprise a lowpass filter configured to pass wavelengths below a specified lowpass cutoff wavelength, while LVF2 144 comprises a highpass filter configured to pass wavelengths above a specified highpass cutoff wavelength. While FIG. 2 shows the incident light impinging LVF1 142 first, followed by LVF2 144, it will be appreciated that the order may be reversed such that the incident light impinges LVF2 144 first, followed by LVF1 142. Further, while the wavelength selector 140 is described in terms of a pair of LVFs, it will be appreciated that the wavelength selector 140 may include more than two LVFs if necessary to achieve a desired pulse shape, and/or to achieve the desired steepness of the slope of the filter and wavelength blocking characteristics.

Figure 3B:
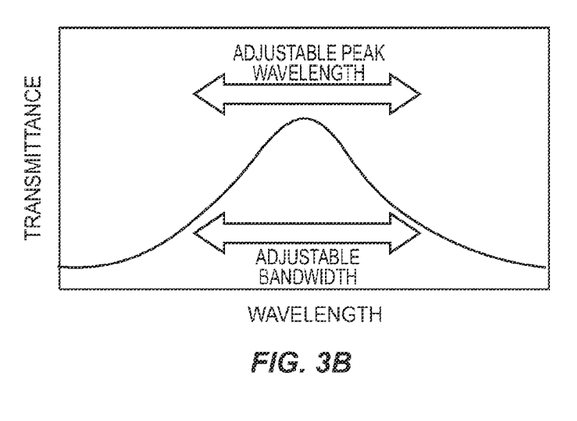

Movement of one or both of the LVFs 142, 144 transverse to the optical path 102 adjusts where the light in the optical path 102 impinges the LVFs 142, 144, and therefore, tunes the center wavelength and passband of the wavelength selector 140, as shown in FIG. 3B. The center wavelength and passband adjustment provided by moving the LVFs 142, 144 transverse to the optical path is over a continuous range of wavelengths, such that a wavelength adjustment of any desired size may be made. As such, the wavelength selector(s) 140 enable substantially infinitely fine adjustment of the center wavelength and/or passband across the range of wavelengths provided by the light source 110, emission wavelength range of the sample, and/or LVF filter coatings. For example, moving both LVF1 142 and LVF2 144 in the same direction transverse to the optical path 102 enables infinitely fine continuous adjustment of the center wavelength, while moving LVF1 142 and LVF2 144 relative to each other transverse to the optical path 102 enables infinitely fine continuous adjustment of the passband. This infinitely fine continuous adjustment is due to the variable coating on the LVFs 142, 144, which enables substantially infinite adjustment of the center wavelength and passband across the range of wavelengths over which the LVFs collectively work. As used herein, infinitely fine means in increments of less than 0.1 nm. Thus, for example, the LVFs 142, 144, working as a pair, are able to adjust the center wavelength and/or passband anywhere over a range of 300 nm to 860 nm in 0.1 nm increments. Because this level of resolution is substantially less than that achievable with conventional microplate readers, one of skill in the art considers this adjustment scheme to be both continuous and infinitely adjustable. Note that, while not shown, each wavelength selector 140 advantageously has an associated movement mechanism, e.g., a direct drive motor, drive motor with suitable gear train, spindle mechanism, or piezoelectric displacement mechanism, etc., configured to move the corresponding LVF traverse to the optical path.

Figures 5A, 5B:
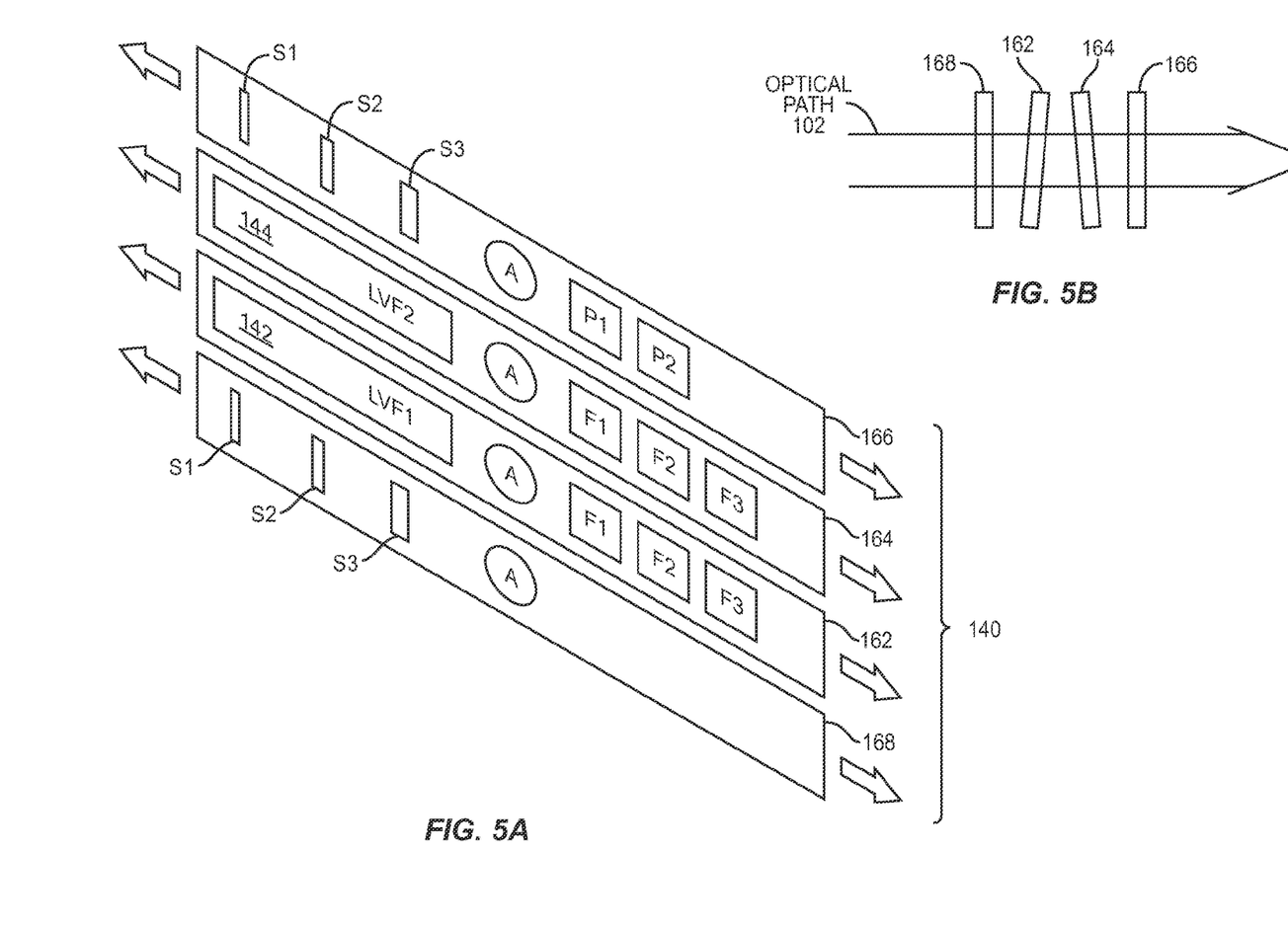
FIGS. 5A and 5B show an exemplary Monochromater Filter Selector (MFS) wavelength selector from an optical path view (5A) and looking down onto the optical path (5B).

While LVFs 142, 144 may be disposed parallel to each other, one or both of LVFs 142, 144 are advantageously not precisely parallel to each other and/or perpendicular the optical path 102 because a slight angle off of parallel improves the optical blocking of the LVF pair and reduces reflections. As a result, LVF1 142 and LVF2 144 are advantageously disposed in the optical path 102 in a non-parallel relationship to each other such that at least one of LVF1 142 and LVF2 144 is offset from perpendicular relative to the optical path 102 by a predetermined angle. For example, the LVFs 142, 144 may be arranged such that the LVFs 142, 144 are at some angle, e.g., 0°-5° relative to each other and/or relative to the optical path 102 (e.g., as shown in FIG. 5B). The LVFs 142, 144 are disposed in the optical path 102 such that one or both of the LVFs 142, 144 may be moved transverse to the optical path 102, with the transverse movement advantageously preserving any offset from perpendicular of the LVFs 142, 144 relative to each other and/or the optical path 102.

The LVFs 142, 144 enable the wavelength selector(s) 140 to provide a wavelength tuning feature for the microplate reader 100. The light transmitted by the wavelength selector(s) 140 can then be used for various optical measurement techniques associated with the microplate reader 100. In exemplary embodiments, the LVFs 142, 144 may be tuned to operate:

at or close to the excitation and/or emission peaks of fluorophores for, e.g., Fluorescence Intensity (FI), Fluorescence Polarization (FP), Time-Resolved Fluorescence (TRF), Fluorescence Resonance Energy Transfer (FRET), or Time-Resolved FRET (TR-FRET);

at or close to energy absorbing and energy emitting wavelengths of dedicated applications, e.g., Alpha Technology (Alpha Screen™, AlphaLSIA™);

at the absorbance (ABS) peaks of analytes for absorbance measurements; or at the emission peak(s) of analytes luminescence at Bioluminescence Resonance Energy Transfer (BRET) measurements or other luminescence applications. It will be appreciated that this list is not exhaustive. It will therefore be appreciated that the LVFs 142, 144 of the disclosed wavelength selector 140 may be tuned to any desired center wavelength and/or passband, and thus are not limited to the testing techniques disclosed herein.

The emission wavelength selector 140B advantageously has the same architecture as the excitation wavelength selector 140A, and is used to allow a certain wavelength of light, or wavelengths of light, to pass through to the detector 120 of the microplate reader 100. While the emission wavelength selector 140B has the same architecture, it may have different operating characteristics, e.g., different low and high pass filter characteristics, different beam shaping characteristics, etc., resulting in different filter characteristics and/or beam shape. It will be appreciated that the LVFs 142A, 144A of the excitation wavelength selector 140A may be moved independently of the LVFs 142B, 144B of the emission wavelength selector 140B if both are present in the microplate reader 100.

The optical system 130 may also include a dichroic 132. The dichroic 132 may be of any conventional design known in the art, such as a thin film coated interference dichroic mirror or a beamsplitter, e.g., a 50:50 beamsplitter. The dichroic 132 may alternatively be advantageously formed from an LVF acting as a tunable dichroic filter, which is referred to herein as a Linear Variable Dichroic Filter (LVDF) 132 to distinguish it from the LVFs in the wavelength selector(s) 140. LVDF 132 reflects light of a certain wavelength or wavelengths down to microplate optical element 130B, which focuses the light on the sample in the microplate well of the microplate 200 or other suitable sample container. On the other side, light exiting the sample in the microplate having a different wavelength than the cutoff wavelength of the LVDF 132 will be transmitted through the LVDF 132 and will enter the emission wavelength selector 140B along path 102. The LVDF 132 may be moved relative to one or both wavelength selectors 140, thereby allowing the use of the LVDF 132 so that a particular dichroic cutoff wavelength can be selected depending on where the light beam impinges the surface of the LVDF 132.

Figure 4:
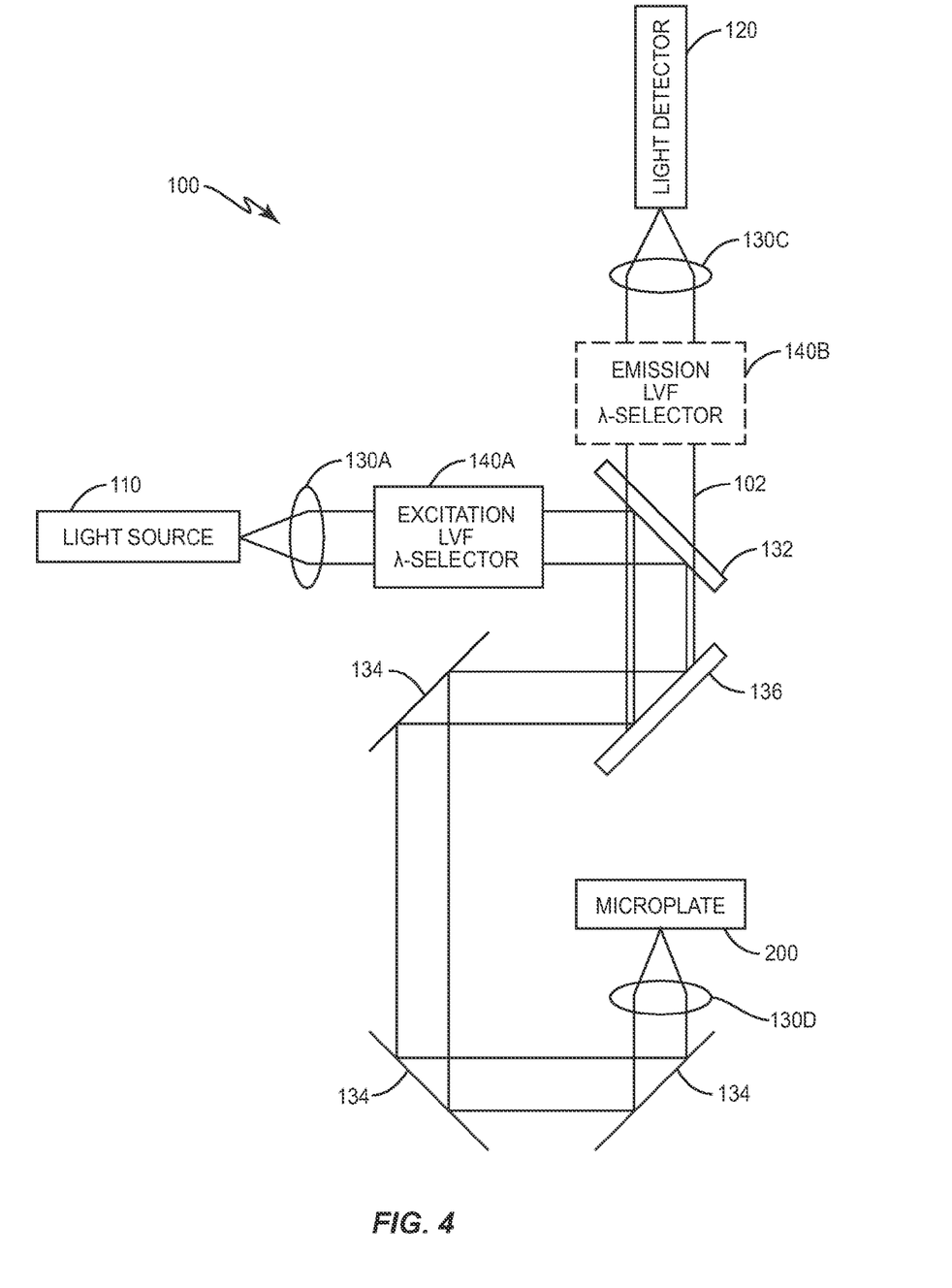
FIG. 4 shows an optical schematic of a microplate reader according to another exemplary embodiment.

While FIG. 1 shows an embodiment where the light from the microplate reader 100 enters and exits the microplate 200 from the top 210 of the microplate 200, in other embodiments the light from the microplate reader 100 enters and exits the microplate 200 from a bottom 220 of the microplate 200, e.g., as shown in FIG. 4. In this embodiment, the optical system 130 may include additional optical elements, e.g., a second microplate optical element 130D and multiple reflectors 134, 136. For example, the second microplate element 130D comprises one or more lenses that focus the collimated light toward the bottom 220 of the microplate 200, e.g., such that the focused light enters the microplate well of the microplate 200 from the bottom 220. The second microplate element 130D also recollimates the light exiting the bottom 220 of the microplate 200. Reflectors 134, 136 reflect the light around the microplate 200 such that the light enters the bottom 220 of the microplate 200, and further reflect the light exiting the microplate 200 back around the microplate 200 to direct the light towards the detector 120. It will be appreciated that layouts other than those shown in FIGS. 1 and 4 may be used to direct the light from the light source 110 toward the top 210 or bottom 220 of the microplate 200. The BMG LABTECH PHERAstarFS™ represents one exemplary bottom reading microplate reader. It will further be appreciated that a single microplate reader 100 may be configured to facilitate both bottom and top reading options. For example, the second microplate optical element 130D and the multiple reflectors 134, 136 of FIG. 4 may be added to the exemplary embodiment of FIG. 1. In this case, reflector 136 may be coupled to a movement mechanism that moves the reflector 136 into the optical path 102 for a bottom reading mode, and out of the optical path 102 for a top reading mode. While not required, the microplate element 130B may also be coupled to a movement mechanism, such that it moves into the optical path 102 when the reflector 136 moves out of the optical path 102, and moves out of the optical path 102 when the reflector 136 moves into the optical path 102.

The wavelength selector(s) 140 may be combined with other optical technologies to improve the performance of the microplate reader 100 in certain measurement modes. For example, slits and large apertures may be used to affect the peak shape of the transmitted light, thereby improving the sensitivity of the microplate reader 100. Polarizers may also or alternatively be incorporated into the microplate reader 100, which allow for the measurement of plane polarized light and enable FP measurements. Various optical filters may additionally or alternatively be used to increase the transmission and/or blocking of light between the excitation and emission stages of the microplate reader 100, which also can improve efficiency in TRF, TR-FRET, FP, and other measurement modes. While the excitation and emission wavelength selectors 140A, 140B generally have the same architecture, they may have different apertures, slits, polarizers, and/or fixed optical filters, where the size of the slit in combination with the wavelength selector 140 influences the steepness of the rising/falling edge of the passband, and/or influences the blocking between the excitation and emission planes.

For example, any number of apertures (of any appropriate shape, e.g., round, elliptical, etc.), slits (a type of narrow aperture), polarizers, and/or fixed optical filters may be coupled with the LVFs 142, 144 to construct a Monochromator Filter Selector (MFS) wavelength selector 140 forming an integrated device that allows the use of various combinations of these technologies as measurement modes dictate. FIG. 5A shows a basic design of one embodiment of an MFS wavelength selector 140 as may be used in the microplate reader 100. The MFS wavelength selector 140 includes four slides 162-168 movable relative to one another. As shown in FIG. 5A by the arrows, slides 162-168 can traverse the optical path 102 in two directions. Light travels through the slides perpendicular to their planes of movement, where the position of each slide determines the impact the MFS wavelength selector 140 has on the light. In the example of FIG. 5A:

Slide 168 contains slits of various widths (S1, S2, S3) and a larger round open aperture (A).
Slide 162 contains LVF1 142, a round aperture (A), and three fixed optical filters (F1, F2, F3).
Slide 164 contains LVF2 144, a round aperture (A), and three fixed optical filters (F1, F2, F3).
Slide 166 contains slits of various widths (S1, S2, S3), a round aperture (A), and two optical polarization filters (P1, P2).

It will be appreciated that FIG. 5A is exemplary, and that other combinations of apertures, slits, filters, LFVs, fixed dichroic mirrors, etc. may be used to form the MFS wavelength selector 140, and that the slides are not limited to the specific numbers of apertures, slits, fixed optical filters, dichroics, or polarizers shown. It will also be appreciated that different apertures, slits, fixed optical filters, dichroics, polarizers, etc., may be used on different slides. While not required, two or more of the slides, e.g., slides 166 and 168, may be moved jointly (e.g., by a common movement mechanism) such that both slides 166, 168 move at the same time and by the same amount. In addition, one or more cylindrical lenses or corresponding mirror systems in path 102 before, within, or after the MFS can be used to shape the light beam through slides 162, 164, 166, 168 to improve overall light transmission for higher energy in the system. Further, it should be noted that the use of the term "fixed" in conjunction with the various fixed optical filters (e.g., F1, F2.) and/or fixed optical polarization filters (e.g., P1, P2) and/or fixed dichroic mirrors (e.g., D1, D2) relates to the optical properties of the corresponding element, not the mechanical properties. Thus, it should be understood that the "fixed" optical filters (e.g., F1, F2) may optionally be removable/replaceable relative to their corresponding slides, but that the optical properties of the element itself are not intentionally variable, and are therefore considered "fixed." Also, slide 168 may sometimes be referred to as beam shaper slide due to its typical function of shaping the physical shape the light entering the MFS wavelength selector 140 from a point upstream of the MFS wavelength selector 140 (at the entry to excitation wavelength selector 140A). Similarly, slide 166 may be referred to as a beam shaper slide due to its typical function of shaping the physical shape of the light exiting the MFS wavelength selector 140.

Figure 6:
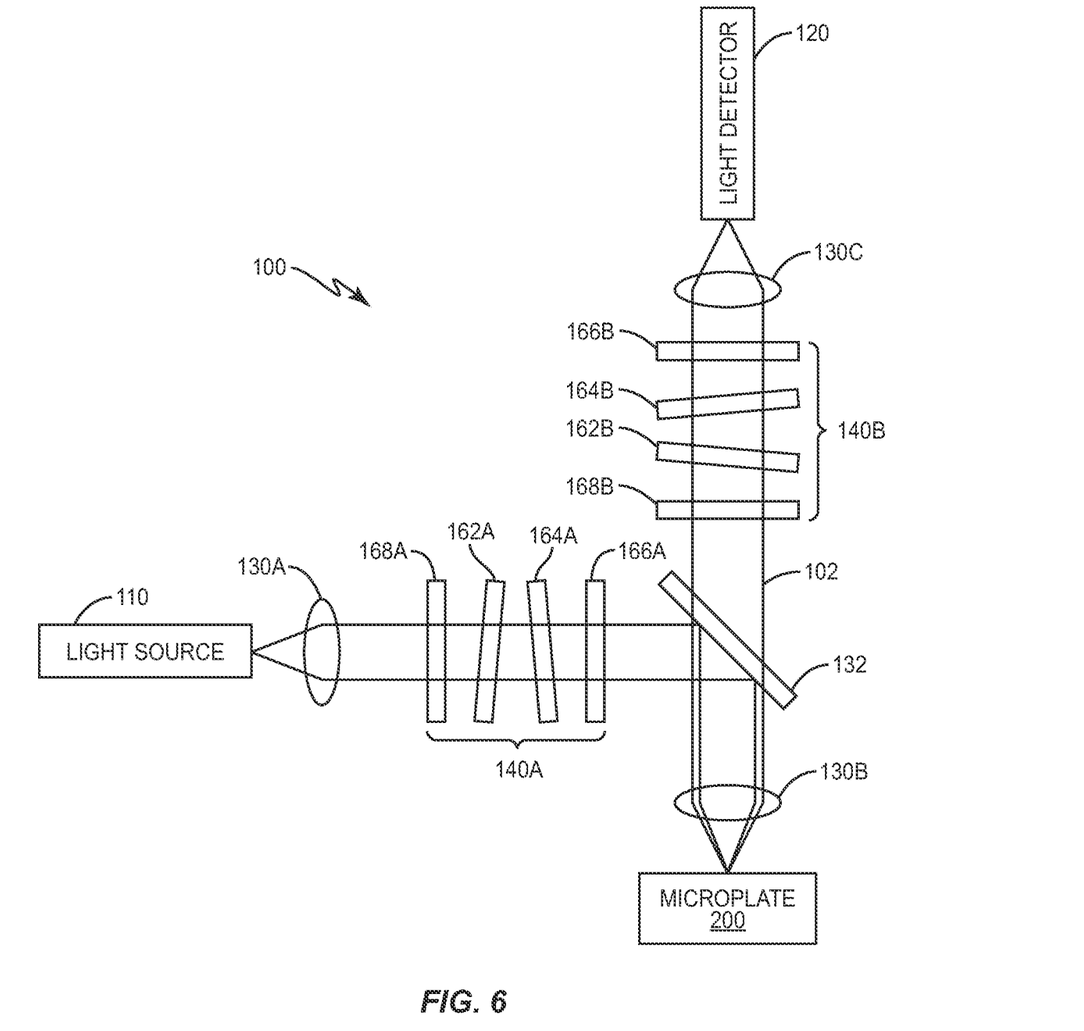
FIG. 6 shows an optical schematic of a microplate reader including multiple wavelength selectors according to one exemplary embodiment.

One MFS wavelength selector 140 may be used in the microplate reader 100, e.g., in the excitation stage (140A) or the emission stage (140B), or multiple MFS wavelength selectors 140 may be used in the microplate reader 100, e.g., one in the excitation stage (140A) and one in the emission stage (140B), as shown in FIG. 6. The MFS wavelength selectors 140 are advantageously arranged orthogonal to one another as shown in the side view of the instrument's optical configuration in FIG. 6. In FIG. 6, the eight slides of the two MFS wavelength selectors 140A, 140B (162A, 164A, 166A, 168A and 162B, 164B, 166, 168B) move in and out of the plane of the illustration. MFS slides 162-168 are adjusted relative to one another to achieve the desired light output of the MFS wavelength selector(s) 140 required by the measurement mode and the light is passed on to the dichroic optical element 132, e.g., LVDF 132.

Figure 7:
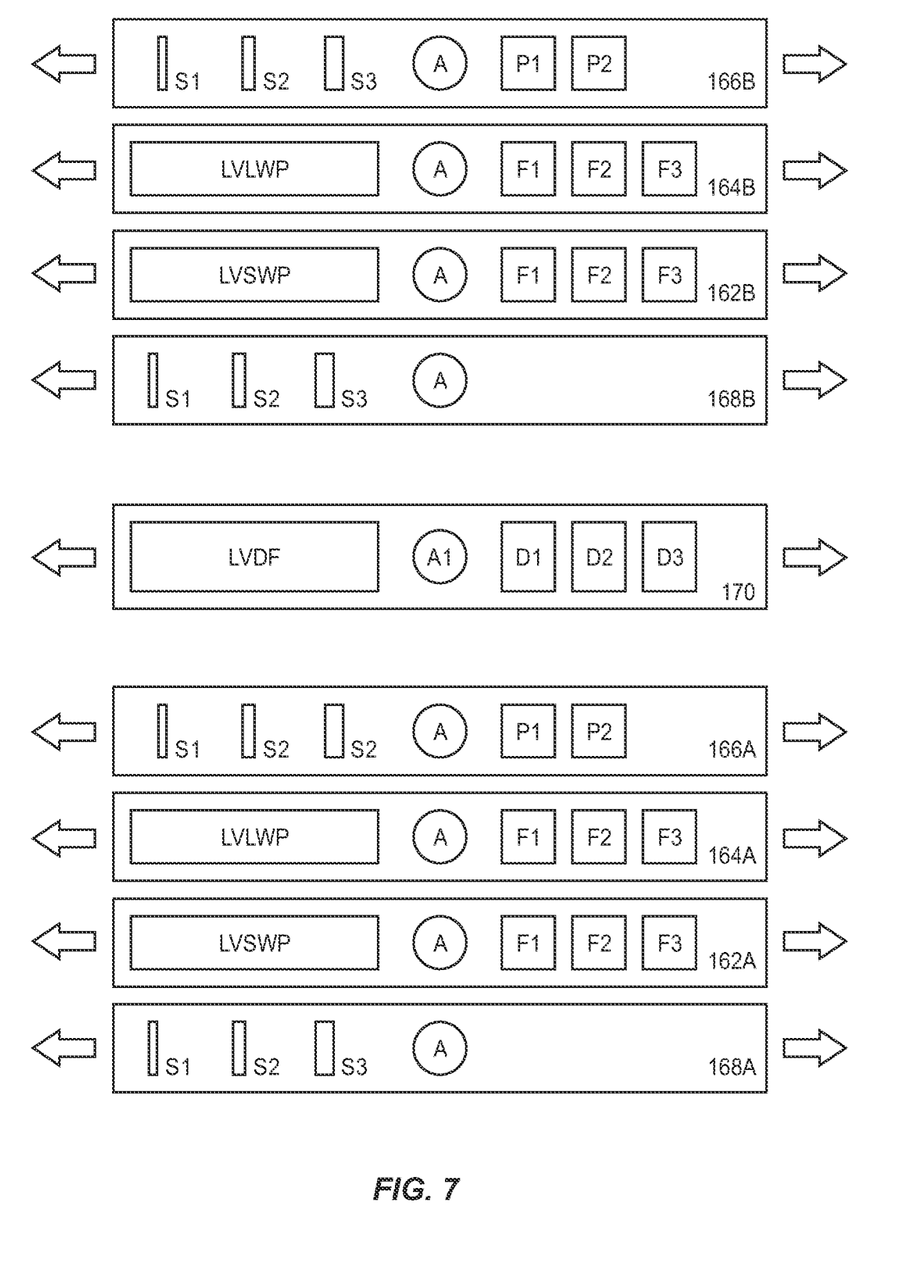
FIG. 7 shows various slides of an exemplary excitation wavelength selector, an exemplary emission wavelength selector, and an exemplary dichroic slide.

FIG. 7 shows examples of the various slides 162-170 of the microplate reader 100. The excitation MFS wavelength selector 140A includes slides 162A, 164A, 166A, 168A, and the emission MFS wavelength selector 140B includes slides 162B, 164B, 166, 168B. Slide 170 is the dichroic slide. As shown in FIG. 7, LVDF 132 may be disposed on a dichroic slide 170, which also optionally contains an aperture (A1), which may advantageously be elliptical in shape, and positions for three fixed dichroic mirrors (D1, D2, D3). The dichroic slide 170 can traverse the optical path 102 relative to one or both wavelength selectors 140, and independently from the wavelength selectors 140, thereby allowing a particular dichroic (D1, D2, D3) to be selected, or, thereby allowing the use of the LVDF 132 so that a particular dichroic cutoff wavelength can be selected depending on where the light beam impinges on the surface of the LVDF 132. By using these slides in combination with one another, any wavelength of ultraviolet, visible, and near-infrared light provided by the light source 110 can be adjusted to a bandwidth, e.g., 4-150 nm, and transmitted to a sample in a microplate well of microplate 200 and/or from the sample in the microplate well to the detector 120. Note that round apertures A of slides 166,168 are advantageously used when a fixed optical filter (e.g., F3 of slide 162) is used instead of LVFs 142,144, unless LVDF 170 is used (in which case a slit such as S1 may advantageously be used).

For example, the slides of the microplate reader 100 may be configurable for FI, TRF, FRET, TR-FRET, or AlphaScreen™. In this case, when LVFs 142, 144 are to be used for a user defined center wavelength and passband using a broadband light source 110, the excitation slide 168A is moved into position to select an appropriate sized slit (S1, S2, S3) for the desired excitation peak shape. Light will pass through the selected slit for further modification in the excitation MFS wavelength selector 140A. LVF1 142A on slide 162A is moved into the proper position to define the falling edge of the transmitted light, and LVF2 144A on slide 164A is moved into the proper position to define the rising edge of the transmitted light. Slide 166A is adjusted for the proper slit width depending on the desired peak shape and blocking efficiency of non-selected wavelengths. The LVDF 132 on dichroic slide 170 is moved into the proper position based on the excitation and emission wavelengths of the analyte to be measured, and the excitation and emission wavelengths and bandpasses selected by the excitation MFS wavelength selector 140A and the emission MFS wavelength selector 140B. The emission slide 168B is moved into position to select an appropriate sized slit (e.g., S1, S2, or S3) for the desired emission peak shape. Light will pass through the selected slit for further modification in the emission MFS wavelength selector 140B. LVF1 142B on slide 162B is moved into the proper position to define the falling edge of the transmitted light, and LVF2 144B on slide 164B is moved into the proper position to define the rising edge of the transmitted light. Slide 166B is adjusted for the proper slit width (S1, S2, S3) depending on the desired peak shape and blocking efficiency of non-selected wavelengths, after which the light propagates to the detector 120.

In the case that an fixed optical filter will be used for excitation, or emission, or both, the appropriate MFS wavelength selector 140 will be adjusted so that the first slide (168A, 168B) in the appropriate MFS wavelength selector 140 will use the aperture (A), and light will pass through the slide unaffected. Depending on the position of the desired fixed optical filter, the appropriate second slide (162A, 162B) or third slide (164A, 164B) of the MFS wavelength selector 140 will be adjusted so light passes through the fixed optical filter and the second slide (162A, 162B) or third slide (164A, 164B) that does not contain the desired fixed optical filter is adjusted to the aperture position (A) so that light passes through it unaffected. The fourth slide (166A, 166B), is adjusted to the aperture position (A) or a slit position (S1, S2, S3). In the case of the excitation MFS wavelength selector 140A, light will be transmitted to dichroic slide 170, or in the case of the emission MFS wavelength selector 140B, light will be transmitted to the detector 120. If the LVDF 132 of the dichroic slide 170 is to be used, then the LVDF 132 is moved into the proper position based on the excitation and emission wavelengths of the analyte to be measured, or, if one of the fixed dichroic mirrors of the dichroic slide 170 is to be used, slide 170 is adjusted so that the appropriate fixed dichroic mirror is in the optical path 102.

Any combination of excitation, emission, and dichroic slides is allowed to be used with any other component providing maximal flexibility and performance from the microplate reader 100.

In another example, the slides of the microplate reader 100 may be configured for FP operation. FP operation is principally the same as FI operation, except that slides 166A and 166B, which contain polarizers, are used. Slide 166A is placed into the optical path 102 of the light beam passing through the excitation MFS wavelength selector 140A so as to plane polarize the light. Slide 166B contains two polarizers, one plane polarizer (P1) and one perpendicular polarizer (P2), which are alternatively inserted into the optical path 102 of the emission MFS wavelength selector 140B before it reaches the detector 102. The FP measurement is obtained by standard polarization data analysis.

In another example, the slides of the microplate reader 100 may be configured for luminescence, e.g., BRET. Operation in luminescence mode typically does not use the excitation MFS wavelength selector 140A. Thus, dichroic slide 170 is adjusted so that aperture (A1) is in the optical path 102. The emission MFS slide 168B is moved into position to select an appropriate sized slit (S1, S2, S3) or the aperture (A) for the desired emission peak shape. Light will pass through the selected slit or aperture for further modification in the emission MFS wavelength selector 140B. The LVF1 142B on slide 162B is moved into the proper position to define the falling edge of the transmitted light, and the LVF2 144B on slide 164B is moved into the proper position to define the rising edge of the transmitted light. Slide 166B is adjusted for the proper slit width (S1, S2, S3) depending on the desired peak shape and blocking efficiency of non-selected wavelengths, after which the light propagates to the detector. In the case that the fixed optical filters (F1, F2, F3) of the emission MFS wavelength selector 140B are to be used, slide 162B or 164B is moved into position to select the proper emission filter while all other slides of the emission MFS wavelength selector 140B are moved to the aperture (A) position.

In another example, the slides of the microplate reader 100 may be configured for absorbance. Absorbance reading is performed using an ultraviolet-visible spectrometer and appropriate optics (not shown) in a similar fashion as other spectrometer-based microplate readers available from BMG LABTECH of Germany. In this case, slides 162, 164, 166, 168 of the excitation MFS wavelength selector 140A are set to large aperture A and slide 170 is set to large aperture A1. As a result, all of the light from light source 110 along path 102 passes through the excitation MFS wavelength selector 140A and can be coupled into the absorbance path positioned after LVDF 170 (not shown).

For purposes of illustration, the slides have been identified by a number/letter combination (e.g., 162A), with the number corresponding to the slide in the wavelength selector 140, and the letter corresponding to the stage (e.g., excitation or emission) of the microplate reader 100. Further, certain optical modifiers are located on certain slides in the illustrative embodiment. For example, the optical polarizers (P1, P2) are located on the "166" slide. However, it should be understood that the optical modifiers may be arranged in any suitable fashion resulting in other inter-slide and/or intra-slide sequences and arrangements. For example, the optical polarizers (P1, P2) could be located on any of the slides in the microplate reader 100 and at different locations on those slides than illustrated.

The various components of the microplate reader 100 are advantageously housed in a common housing so as to form a compact laboratory instrument, where the microplate 200 may be inserted into the housing to properly align the microplate well with the light. Of course, the light source 110 and/or light detector 120 may or may not be integrated therein as is desired. As is conventional, the output from the light detector 120 is advantageously routed to a suitable computing device for analysis.

Unlike conventional microplate readers, which have slit adjustability for a few relatively widely spaced apart discrete bandwidths, e.g., 8 nm, 12 nm, and 20 nm, or limited ranges for the bandwidth, e.g., 5-25 nm, the use of the LVFs 142, 144 as disclosed herein enables the continuous adjustment of the passband (and center wavelength) across a wider range of wavelengths, e.g., 4-150 nm. Further, the microplate reader 100 disclosed herein may also advantageously provide a combined LVF monochromater and spectrometer into a single microplate reader. Thus, in preferred embodiments, the microplate reader 100 allows for different types of measurements on a well of the microplate 200, with one measurement being performed with a given pair of LVFs 142,144 disposed in the optical path, and the other measurement being performed with the pair of LVFs 142,144 not being in the optical path, all without changing a geometry of the optical path 102 from a point upstream of the excitation wavelength selector 140A (at the entry to excitation wavelength selector 140A) to a point downstream of the emission wavelength selector (140B)(at the exit of emission wavelength selector 140B). The "geometry" of the optical path refers to the geometric routing of the optical path, not the contents of the optical path (i.e., not the particular components of the optical path or the shape of the light beam in the path). Thus, the geometry of the optical path is not changed when any or all of:

slide 162 is moved from where LVF1 142 is in the optical path to where fixed optical filter F2 is in the optical path;

slide 164 is moved from where fixed optical filter F3 is in the optical path to where LVF2 144 is in the optical path;

LVDF slide 170 is moved from where LVDF 132 is in the optical path to where fixed dichroic mirror D1 is in the optical path;

beam shaper slide 168 is moved from where round aperture A is in the optical path to where slit S2 is in the optical path;

a different light source 110 or detector 120 are used at the same light source/detector location microplate 200 is moved so a different well is at the relevant measurement location.

For example, in a first measurement, the slides 162,164 may be positioned so that LVFs 142,144 are in the optical path 102 through the wavelength selector 140A, as are slit S1 of slide 166 and slit S2 of slide 168. Then, without changing the geometry of the optical path 102, slides 162,164 may be moved so that large aperture A of slide 164 and filter F3 of slide 162 are in the optical path 102, and a second measurement taken. Of course, the sequence could be reversed, and other filters, polarizers, etc. could be alternatively/additionally used. The same lack of change to the geometry of the optical path holds true if the slide changes take place alternatively or additionally in second wavelength selector 140B, or in dichroic slide 170.

The discussion above has been in the context of the LVFs 142,144 being on slides 162-168 along with various apertures, slits, filters, LFVs, fixed dichroic mirrors, fixed optical polarization filters, etc., and with these slides moving linearly. However, such is not required in all embodiments. In some embodiments, rotary disks (whole or partial) may be used instead of slides 162-168. Such rotary disks may be rotated by suitable means (e.g., stepper motors, gear trains, etc.) so that the desired optical component (e.g., LVF 142, or filter F2, etc.) is disposed in the optical path. The term "movable frame" will be used to encompass both such slides and such rotary disks.

One MFS wavelength selector 140 may be used in the microplate reader 100, e.g., in the excitation stage (140A) or the emission stage (140B), or multiple MFS wavelength selectors 140 may be used in the microplate reader 100, e.g., one in the excitation stage (140A) and one in the emission stage (140B), as shown in FIG. 6. The MFS wavelength selectors 140 are advantageously arranged orthogonal to one another as shown in the side view of the instrument's optical configuration in FIG. 6. In FIG. 6, the eight slides of the two MFS wavelength selectors 140A, 140B (162A, 164A, 166A, 168A and 162B, 164B, 166B, 168B) move in and out of the plane of the illustration. MFS slides 162-168 are adjusted relative to one another to achieve the desired light output of the MFS wavelength selector(s) 140 required by the measurement mode and the light is passed on to the dichroic optical element 132, e.g., LVDF 132.

Figure 8:
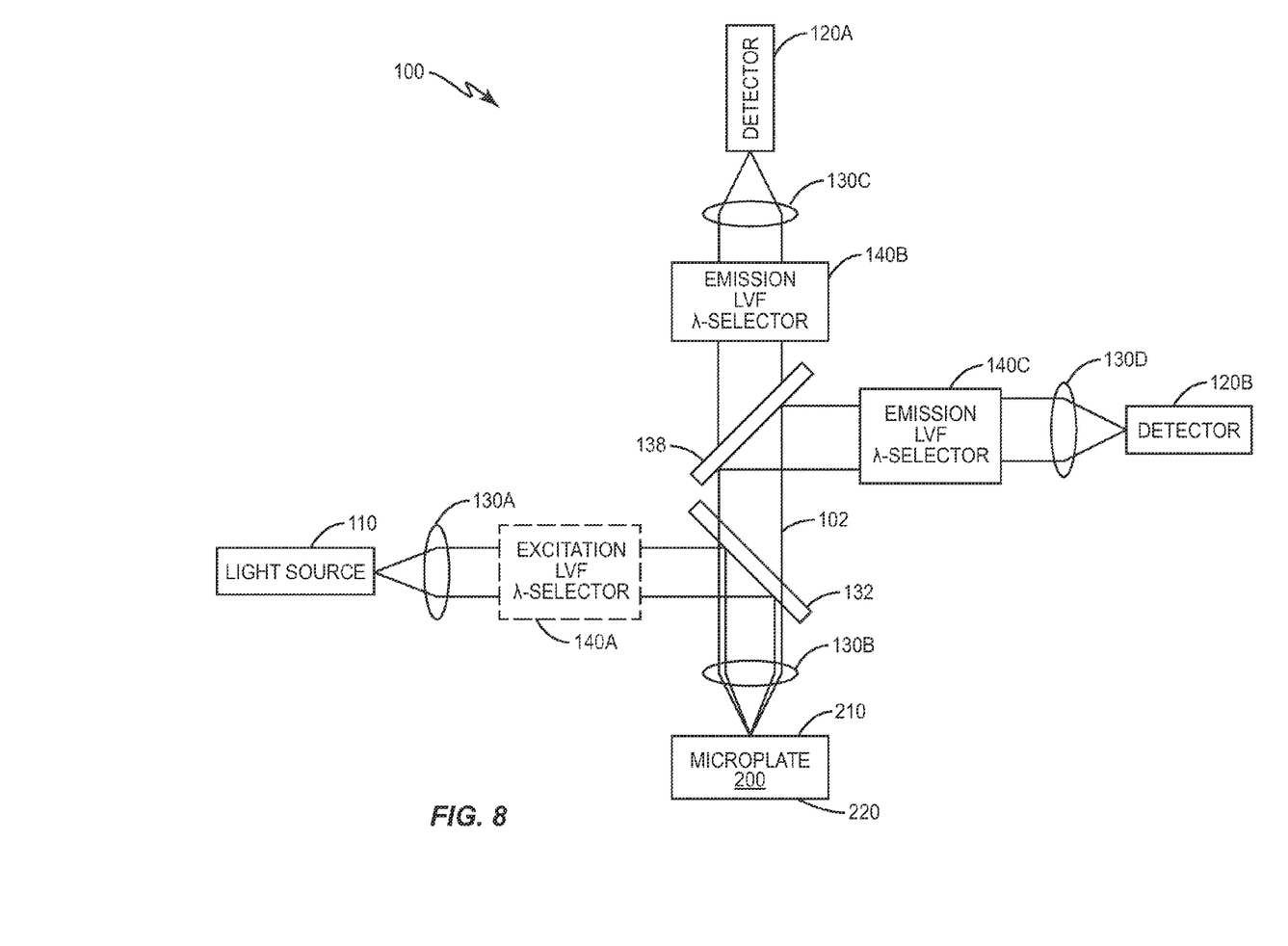
FIG. 8 shows an optical schematic of a microplate reader according to another exemplary embodiment.

The embodiments of FIGS. 1, 4, and 6 discuss implementations having one wavelength selector 140A in the excitation path and/or one wavelength selector 140B in the emission path. The microplate reader 100 disclosed herein is not so limited, and may, for example, include multiple wavelength selectors 140 in the excitation and/or emission paths. For example, the emission path may include multiple wavelength selectors 140B, 140C to implement simultaneous dual emission operations, as shown in FIG. 8. In this example, detector 120 comprises a detector 120A (and the associated detector optical element 130C) for the first emission wavelength selector 140B and a detector 120B (and the associated detector optical element 130D) for the second emission wavelength selector 140C. The light along the optical path from the microplate 200 is split, e.g., by a beamsplitter according to a predetermined split ratio. As a result, a first portion of the light from the microplate 200 passes through emission wavelength selector 140B to be detected by detector 120A, while a second portion of the light from the microplate 200 passes through emission wavelength selector 140C to be detected by detector 120B. In addition, beamsplitter 138 may comprise a dichroic mirror with wavelength dependent characteristics to separate light of different wavelengths to emission wavelength selector 140B and emission wavelength selector 140C.

The discussion above has generally assumed that each of movable frames (e.g., slides) 162,164 in each of wavelength selectors 140A, 140B, 140C, each include an LVF (142, etc.) and at least one of an aperture (A or S1, S2, etc.), a fixed optical filter (F1, etc.), and an optical polarization filter (P1, etc.) disposed thereon. However, in some embodiments, one of the movable frames 162,164 of any or all of the wavelength selectors may have an LVF disposed thereon without any aperture, fixed optical filter, or optical polarization filter, while the other movable frame of that wavelength selector may have both an LVF and at least one of an aperture, a fixed optical filter, and an optical polarization filter disposed thereon. In still other embodiments, which are believed to be less flexible in functionality, some or all of the wavelength selectors may have both movable frames 162,164 that have LVFs disposed thereon, but without any apertures, fixed optical filters, or optical polarization filters disposed thereon.

The disclosure of all patents and patent publications mentioned above are incorporated herein by reference in their entirety.

The present invention may, of course, be carried out in other ways than those specifically set forth herein without departing from essential characteristics of the invention. The present embodiments are to be considered in all respects as illustrative and not restrictive, and all changes coming within the meaning and equivalency range of the appended claims are intended to be embraced therein.

What is claimed is:

1. A microplate reader comprising:
a light source configured to emit light at one or more wavelengths;
a detector configured to detect incident light;
an optical system comprising a plurality of optical elements configured to guide light emitted by the light source along an optical path of the microplate reader from the light source to a microplate, and from the microplate to the detector;
a first wavelength selector disposed optically between the light source and the microplate, the first wavelength selector comprising a first pair of linear variable filters disposed in the optical path, the first pair of linear variable filters comprising first and second linear variable filters, the first linear variable filter movable transverse to the optical path and relative to the second linear variable filter;
a second wavelength selector disposed optically between the microplate and the detector, the second wavelength selector comprising a second pair of linear variable filters disposed in the optical path, the second pair of linear variable filters comprising third and fourth linear variable filters, the third linear variable filter movable transverse to the optical path and relative to the fourth linear variable filter;
a dichroic optical element disposed between the light source, the detector, and the microplate so as to direct the light emitted by the light source to the microplate, and to direct the light from the microplate to the detector; wherein the dichroic optical element comprises a fifth linear variable filter disposed on a fifth moveable frame, the fifth moveable frame further having at least one of an aperture and a fixed dichroic mirror disposed thereon;
wherein the first linear variable filter is disposed on a first moveable frame, the first movable frame further having at least one of an aperture, a fixed optical filter, and an optical polarization filter disposed thereon;
wherein the second linear variable filter is disposed on a second moveable frame, distinct from the first movable frame, the second movable frame further having at least one of an aperture, a fixed optical filter, and an optical polarization filter disposed thereon;
wherein the third linear variable filter is disposed on a third moveable frame, the third movable frame further having at least one of an aperture, a fixed optical filter, and an optical polarization filter disposed thereon;
wherein the fourth linear variable filter is disposed on a fourth moveable frame, distinct from the third movable frame, the fourth movable frame further having at least one of an aperture, a fixed optical filter, and an optical polarization filter disposed thereon;
wherein the first wavelength selector is configured such that movement of at least one of the first and second linear variable filters, transverse to the optical path, adjusts at least one of a first center wavelength and a first bandwidth of the first wavelength selector over a continuous range of wavelengths;
wherein the second wavelength selector is configured such that movement of at least one of the third and fourth linear variable filters transverse to the optical path adjusts at least one of a second center wavelength and a second bandwidth of the second wavelength selector over the continuous range of wavelengths;

wherein a first variably sized set of linear variable filters includes one or more of the first, second, third, fourth, and fifth linear variable filters;

wherein the microplate reader is configured such that at least one of (a) and (b) are true:
  (a) the microplate reader is configured to perform both (i) and (ii) without changing a geometry of the optical path from a point upstream of the first wavelength selector through to a point downstream of the second wavelength selector:
    (i) take a first measurement based on light detected from a well of the microplate while all members of the first set of linear variable filters are disposed in the optical path;
    (ii) take a second subsequent measurement based on light detected from the well of the microplate while at least one member of the first set of linear variable filters is disposed not in the optical path;
  (b) the microplate reader is configured to perform both (iii) and (iv) without changing a geometry of the optical path from a point upstream of the first wavelength selector through to a point downstream of the second wavelength selector:
    (iii) take a first measurement based on light detected from a well of the microplate while at least one member of the first set of linear variable filters is disposed not in the optical path;
    (iv) take a second subsequent measurement based on light detected from the well of the microplate while all members of the first set of linear variable filters are disposed in the optical path.

2. The microplate reader of claim 1, wherein the first, second, third, fourth, and fifth moveable frames are linearly movable slides.

3. The microplate reader of claim 1:
wherein one or more of the plurality of optical elements in the optical system are configured to direct the light emitted by the light source toward a first side of the microplate, and to direct light exiting the first side of the microplate to the detector;
wherein the first side is one of a top of the microplate and a bottom of the microplate.

4. The microplate reader of claim 1, wherein the first wavelength selector is configured such that the first central wavelength of the first wavelength selector is infinitely adjustable across the range of wavelengths by moving both the first and second linear variable filters transversely to the optical path in the same direction.

5. The microplate reader of claim 4, wherein the second wavelength selector is configured such that the second central wavelength of the second wavelength selector is infinitely adjustable across the range of wavelengths by moving both the third and fourth linear variable filters transversely to the optical path in the same direction.

6. The microplate reader of claim 1, wherein the first wavelength selector is configured such that the first bandwidth of the first wavelength selector is infinitely adjustable across the range of wavelengths by moving one of the first and second linear variable filters relative to the other transversely to the optical path.

7. The microplate reader of claim 6, wherein the second wavelength selector is configured such that the second bandwidth of the second wavelength selector is infinitely adjustable across the range of wavelengths by moving one of the third and fourth linear variable filters relative to the other transversely to the optical path.

8. A microplate reader comprising:
a light source configured to emit light at one or more wavelengths;
a detector configured to detect incident light;
an optical system comprising a plurality of optical elements configured to guide light emitted by the light source along an optical path of the microplate reader from the light source to a microplate, and from the microplate to the detector;
a first wavelength selector disposed optically between the light source and the microplate, the first wavelength selector comprising a first pair of linear variable filters disposed in the optical path, the first pair of linear variable filters comprising first and second linear variable filters, the first linear variable filter movable transverse to the optical path and relative to the second linear variable filter;
a second wavelength selector disposed optically between the microplate and the detector, the second wavelength selector comprising a second pair of linear variable filters disposed in the optical path, the second pair of linear variable filters comprising third and fourth linear variable filters, the third linear variable filter movable transverse to the optical path and relative to the fourth linear variable filter;
a dichroic optical element disposed between the light source, the detector, and the microplate so as to direct the light emitted by the light source to the microplate, and to direct the light from the microplate to the detector; wherein the dichroic optical element comprises a fifth linear variable filter disposed on a fifth moveable frame, the fifth moveable frame further having at least one of an aperture and a fixed dichroic mirror disposed thereon;
wherein the first linear variable filter is disposed on a first moveable frame, the first movable frame further having at least one of an aperture, a fixed optical filter, and an optical polarization filter disposed thereon;
wherein the second linear variable filter is disposed on a second moveable frame, distinct from the first movable frame, the second movable frame further having at least one of an aperture, a fixed optical filter, and an optical polarization filter disposed thereon;
wherein the third linear variable filter is disposed on a third moveable frame, the third movable frame further having at least one of an aperture, a fixed optical filter, and an optical polarization filter disposed thereon;
wherein the fourth linear variable filter is disposed on a fourth moveable frame, distinct from the third movable frame, the fourth movable frame further having at least one of an aperture, a fixed optical filter, and an optical polarization filter disposed thereon;
wherein the first wavelength selector is configured such that movement of at least one of the first and second linear variable filters, transverse to the optical path, adjusts at least one of a first center wavelength and a first bandwidth of the first wavelength selector over a continuous range of wavelengths;
wherein the second wavelength selector is configured such that movement of at least one of the third and fourth linear variable filters transverse to the optical path adjusts at least one of a second center wavelength and a second bandwidth of the second wavelength selector over the continuous range of wavelengths;
wherein the first and second linear variable filters are disposed in the optical path in a non-parallel relationship to each other such that at least one of the first and second linear variable filters is offset from perpendicular relative to the optical path by a predetermined angle; and wherein the movement of at least one of the first and second linear variable filters transverse to the optical path preserves the relative offset between the first and second linear variable filters.

9. The microplate reader of claim 8, wherein the first wavelength selector is configured such that the first central wavelength of the first wavelength selector is infinitely adjustable across the range of wavelengths by moving both the first and second linear variable filters transversely to the optical path in the same direction.

10. The microplate reader of claim 8, wherein the first wavelength selector is configured such that the first bandwidth of the first wavelength selector is infinitely adjustable across the range of wavelengths by moving one of the first and second linear variable filters relative to the other transversely to the optical path.

11. A microplate reader comprising:
a light source configured to emit light at one or more wavelengths;
a detector configured to detect incident light;
an optical system comprising a plurality of optical elements configured to guide light emitted by the light source along an optical path of the microplate reader from the light source to a microplate, and from the microplate to the detector;
a first wavelength selector disposed optically between the light source and the microplate, the first wavelength selector comprising a first pair of linear variable filters disposed in the optical path, the first pair of linear variable filters comprising first and second linear variable filters, the first linear variable filter movable transverse to the optical path and relative to the second linear variable filter;
a second wavelength selector disposed optically between the microplate and the detector, the second wavelength selector comprising a second pair of linear variable filters disposed in the optical path, the second pair of linear variable filters comprising third and fourth linear variable filters, the third linear variable filter movable transverse to the optical path and relative to the fourth linear variable filter;
a dichroic optical element disposed between the light source, the detector, and the microplate so as to direct the light emitted by the light source to the microplate, and to direct the light from the microplate to the detector; wherein the dichroic optical element comprises a fifth linear variable filter disposed on a fifth moveable frame, the fifth moveable frame further having at least one of an aperture and a fixed dichroic mirror disposed thereon;
wherein the first linear variable filter is disposed on a first moveable frame, the first movable frame further having at least one of an aperture, a fixed optical filter, and an optical polarization filter disposed thereon;
wherein the second linear variable filter is disposed on a second moveable frame, distinct from the first movable frame, the second movable frame further having at least one of an aperture, a fixed optical filter, and an optical polarization filter disposed thereon;
wherein the third linear variable filter is disposed on a third moveable frame, the third movable frame further having at least one of an aperture, a fixed optical filter, and an optical polarization filter disposed thereon;
wherein the fourth linear variable filter is disposed on a fourth moveable frame, distinct from the third movable frame, the fourth movable frame further having at least one of an aperture, a fixed optical filter, and an optical polarization filter disposed thereon;
wherein the first wavelength selector is configured such that movement of at least one of the first and second linear variable filters, transverse to the optical path, adjusts at least one of a first center wavelength and a first bandwidth of the first wavelength selector over a continuous range of wavelengths;
wherein the second wavelength selector is configured such that movement of at least one of the third and fourth linear variable filters transverse to the optical path adjusts at least one of a second center wavelength and a second bandwidth of the second wavelength selector over the continuous range of wavelengths;
wherein the third and fourth linear variable filters are disposed in the optical path in a non-parallel relationship to each other such that at least one of the third and fourth linear variable filters is offset from perpendicular relative to the optical path by a predetermined angle; and
wherein the movement of at least one of the third and fourth linear variable filters transverse to the optical path preserves the relative offset between the third and fourth linear variable filters.

12. The microplate reader of claim 11, wherein the second wavelength selector is configured such that the second central wavelength of the second wavelength selector is infinitely adjustable across the range of wavelengths by moving both the third and fourth linear variable filters transversely to the optical path in the same direction.

13. The microplate reader of claim 11, wherein the second wavelength selector is configured such that the second bandwidth of the second wavelength selector is infinitely adjustable across the range of wavelengths by moving one of the third and fourth linear variable filters relative to the other transversely to the optical path.

14. A method of adjusting optical properties of a microplate reader comprising a light source, a detector, and an optical system comprising a plurality of optical elements configured to guide light emitted by the light source along an optical path of the microplate reader from the light source to a microplate, and from the microplate to the detector, the method comprising:
adjusting at least one of a first center wavelength and a first bandwidth of a first wavelength selector over a continuous range of wavelengths by moving at least one of a first linear variable filter and a second linear variable filter transverse to the optical path;
adjusting at least one of a second center wavelength and a second bandwidth of a second wavelength selector over a continuous range of wavelengths by moving at least one of a third linear variable filter and a fourth linear variable filter transverse to the optical path;
adjusting a dichroic optical element;
wherein the first wavelength selector comprises a first pair of linear variable filters and is disposed in the optical path between the light source and a microplate, wherein:
the first pair of linear variable filters comprises the first and second linear variable filters, with at least the first linear variable filter movable transverse to the optical path and relative to the second linear variable filter;

wherein the first linear variable filter is disposed on a first moveable frame, the first movable frame further having at least one of an aperture, a fixed optical filter, and an optical polarization filter disposed thereon;

wherein the second linear variable filter is disposed on a second moveable frame, distinct from the first movable frame, the second movable frame further having at least one of an aperture, a fixed optical filter, and an optical polarization filter disposed thereon;

wherein the second wavelength selector comprises a second pair of linear variable filters and is disposed in the optical path between the microplate and the detector, wherein:

the second pair of linear variable filters comprises the third and fourth linear variable filters, with at least the third linear variable filter movable transverse to the optical path and relative to the fourth linear variable filter;

wherein the third linear variable filter is disposed on a third moveable frame, the third movable frame further having at least one of an aperture, a fixed optical filter, and an optical polarization filter disposed thereon;

wherein the fourth linear variable filter is disposed on a fourth moveable frame, distinct from the third movable frame, the fourth movable frame further having at least one of an aperture, a fixed optical filter, and an optical polarization filter disposed thereon;

wherein the dichroic optical element is optically positioned between the light source, the detector, and the microplate so as to direct the light emitted by the light source to the microplate, and to direct the light from the microplate to the detector; wherein the dichroic optical element comprises a fifth linear variable filter disposed on a fifth moveable frame, the fifth moveable frame further having at least one of an aperture and a fixed dichroic mirror disposed thereon;

wherein a first variably sized set of linear variable filters includes one or more of the first, second, third, fourth, and fifth linear variable filters;

the method further comprising at least one of process (a) and process (b);

wherein process (a) comprises:

(i) detecting light from a well of the microplate while all members of the first set of linear variable filters are disposed in the optical path;

(ii) after (i), without changing a geometry of the optical path from a point upstream of the first wavelength selector through to a point downstream of the second wavelength selector, detecting light from the well of the microplate while at least one member of the first set of linear variable filters is disposed not in the optical path;

wherein process (b) comprises:

(iii) detecting light from a well of the microplate while at least one member of the first set of linear variable filters is disposed not in the optical path;

(iv) after (iii), without changing a geometry of the optical path from a point upstream of the first wavelength selector through to a point downstream of the second wavelength selector, detecting light from the well of the microplate while all members of the first set of linear variable filters are disposed in the optical path.

15. The microplate reader of claim 14, further comprising:

directing, via the optical system, the light emitted by the light source toward a first side of the microplate; and directing, via the optical system light exiting the first side of the microplate to the detector;

wherein the first side of the microplate is one of a top of the microplate and a bottom of the microplate.

16. The method of claim 14, wherein the adjusting at least one of a first center wavelength and a first bandwidth of the first wavelength selector comprises infinitely adjusting the first center wavelength by moving both the first and second linear variable filters transversely to the optical path in the same direction.

17. The method of claim 14, wherein the adjusting at least one of a first center wavelength and a first bandwidth of the first wavelength selector comprises infinitely adjusting the first bandwidth by moving one of the first and second linear variable filters relative to the other transversely to the optical path.

18. The method of claim 14, wherein the second wavelength selector comprises a first emission wavelength selector disposed between the microplate and the detector, the method further comprising:

utilizing a second emission wavelength selector to take one or more measurements from the microplate, wherein the second emission wavelength selector comprising a third pair of linear variable filters and disposed between the microplate and a second detector;

adjusting the fifth linear variable filter to direct light from the microplate to the first and second emission wavelength selectors simultaneously.

19. A method of adjusting optical properties of a microplate reader comprising a light source, a detector, and an optical system comprising a plurality of optical elements configured to guide light emitted by the light source along an optical path of the microplate reader from the light source to a microplate, and from the microplate to the detector, the method comprising:

adjusting at least one of a first center wavelength and a first bandwidth of a first wavelength selector over a continuous range of wavelengths by moving at least one of a first linear variable filter and a second linear variable filter transverse to the optical path;

adjusting at least one of a second center wavelength and a second bandwidth of a second wavelength selector over a continuous range of wavelengths by moving at least one of a third linear variable filter and a fourth linear variable filter transverse to the optical path;

adjusting a dichroic optical element;

wherein the first wavelength selector comprises a first pair of linear variable filters and is disposed in the optical path between the light source and a microplate, wherein:

the first pair of linear variable filters comprises the first and second linear variable filters, with at least the first linear variable filter movable transverse to the optical path and relative to the second linear variable filter;

wherein the first linear variable filter is disposed on a first moveable frame, the first movable frame further having at least one of an aperture, a fixed optical filter, and an optical polarization filter disposed thereon;

wherein the second linear variable filter is disposed on a second moveable frame, distinct from the first movable frame, the second movable frame further having at least one of an aperture, a fixed optical filter, and an optical polarization filter disposed thereon;

wherein the second wavelength selector comprises a second pair of linear variable filters and is disposed in the optical path between the microplate and the detector, wherein:

the second pair of linear variable filters comprises the third and fourth linear variable filters, with at least the third linear variable filter movable transverse to the optical path and relative to the fourth linear variable filter;

wherein the third linear variable filter is disposed on a third moveable frame, the third movable frame further having at least one of an aperture, a fixed optical filter, and an optical polarization filter disposed thereon;

wherein the fourth linear variable filter is disposed on a fourth moveable frame, distinct from the third movable frame, the fourth movable frame further having at least one of an aperture, a fixed optical filter, and an optical polarization filter disposed thereon;

wherein the dichroic optical element is optically positioned between the light source, the detector, and the microplate so as to direct the light emitted by the light source to the microplate, and to direct the light from the microplate to the detector; wherein the dichroic optical element comprises a fifth linear variable filter disposed on a fifth moveable frame, the fifth moveable frame further having at least one of an aperture and a fixed dichroic mirror disposed thereon;

wherein the first and second linear variable filters are disposed in the optical path in a non-parallel relationship to each other such that at least one of the first and second linear variable filters is offset from perpendicular relative to the optical path by a predetermined angle;

wherein the moving at least one of the first and second linear variable filters comprises moving at least one of the first and second linear variable filters transverse to the optical path while preserving the relative offset between the first and second linear variable filters.

20. The method of claim 19, wherein the adjusting at least one of a first center wavelength and a first bandwidth of the first wavelength selector comprises infinitely adjusting the first center wavelength by moving both the first and second linear variable filters transversely to the optical path in the same direction.

21. The method of claim 19, wherein the adjusting at least one of a first center wavelength and a first bandwidth of the first wavelength selector comprises infinitely adjusting the first bandwidth by moving one of the first and second linear variable filters relative to the other transversely to the optical path.

22. A method of adjusting optical properties of a microplate reader comprising a light source, a detector, and an optical system comprising a plurality of optical elements configured to guide light emitted by the light source along an optical path of the microplate reader from the light source to a microplate, and from the microplate to the detector, the method comprising:

adjusting at least one of a first center wavelength and a first bandwidth of a first wavelength selector over a continuous range of wavelengths by moving at least one of a first linear variable filter and a second linear variable filter transverse to the optical path;

adjusting at least one of a second center wavelength and a second bandwidth of a second wavelength selector over a continuous range of wavelengths by moving at least one of a third linear variable filter and a fourth linear variable filter transverse to the optical path;

adjusting a dichroic optical element;

wherein the first wavelength selector comprises a first pair of linear variable filters and is disposed in the optical path between the light source and a microplate, wherein:

the first pair of linear variable filters comprises the first and second linear variable filters, with at least the first linear variable filter movable transverse to the optical path and relative to the second linear variable filter;

wherein the first linear variable filter is disposed on a first moveable frame, the first movable frame further having at least one of an aperture, a fixed optical filter, and an optical polarization filter disposed thereon;

wherein the second linear variable filter is disposed on a second moveable frame, distinct from the first movable frame, the second movable frame further having at least one of an aperture, a fixed optical filter, and an optical polarization filter disposed thereon;

wherein the second wavelength selector comprises a second pair of linear variable filters and is disposed in the optical path between the microplate and the detector, wherein:

the second pair of linear variable filters comprises the third and fourth linear variable filters, with at least the third linear variable filter movable transverse to the optical path and relative to the fourth linear variable filter;

wherein the third linear variable filter is disposed on a third moveable frame, the third movable frame further having at least one of an aperture, a fixed optical filter, and an optical polarization filter disposed thereon;

wherein the fourth linear variable filter is disposed on a fourth moveable frame, distinct from the third movable frame, the fourth movable frame further having at least one of an aperture, a fixed optical filter, and an optical polarization filter disposed thereon;

wherein the dichroic optical element is optically positioned between the light source, the detector, and the microplate so as to direct the light emitted by the light source to the microplate, and to direct the light from the microplate to the detector; wherein the dichroic optical element comprises a fifth linear variable filter disposed on a fifth moveable frame, the fifth moveable frame further having at least one of an aperture and a fixed dichroic mirror disposed thereon;

wherein the third and fourth linear variable filters are disposed in the optical path in a non-parallel relationship to each other such that at least one of the third and fourth linear variable filters is offset from perpendicular relative to the optical path by a predetermined angle;

wherein the moving at least one of the third and fourth linear variable filters comprises moving at least one of the third and fourth linear variable filters transverse to the optical path while preserving the relative offset between the third and fourth linear variable filters.

* * * * *